United States Patent
Nair et al.

(10) Patent No.: US 8,444,661 B2
(45) Date of Patent: May 21, 2013

(54) UNFOLDING BALLOON CATHETER FOR PROXIMAL EMBOLUS PROTECTION

(75) Inventors: Ajitkumar B. Nair, Fremont, CA (US); Kamal Ramzipoor, Fremot, CA (US); Tra Huong Ngo, San Jose, CA (US); Hieu T. Nguyen, San Jose, CA (US); Maggie Le, San Jose, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 1238 days.

(21) Appl. No.: 11/770,023

(22) Filed: Jun. 28, 2007

(65) Prior Publication Data
US 2007/0249998 A1 Oct. 25, 2007

Related U.S. Application Data

(63) Continuation-in-part of application No. 10/690,004, filed on Oct. 21, 2003, now abandoned.

(51) Int. Cl.
*A61B 17/22* (2006.01)
*A61D 1/02* (2006.01)

(52) U.S. Cl.
USPC ....................................................... 606/159

(58) Field of Classification Search
USPC ......... 606/113, 159, 114, 127, 128, 190–200; 623/1.11; 604/104, 509; 600/116
See application file for complete search history.

(56) References Cited

U.S. PATENT DOCUMENTS

| | | | |
|---|---|---|---|
| 4,243,040 A * | 1/1981 | Beecher | 606/127 |
| 4,469,100 A * | 9/1984 | Hardwick | 606/127 |
| 4,881,547 A * | 11/1989 | Danforth | 606/194 |
| 5,320,634 A * | 6/1994 | Vigil et al. | 606/159 |
| 5,695,519 A | 12/1997 | Summers et al. | |
| 5,772,609 A | 6/1998 | Nguyen et al. | |
| 5,947,995 A | 9/1999 | Samuels | |
| 6,001,118 A | 12/1999 | Daniel et al. | |
| 6,139,510 A | 10/2000 | Palermo | |
| 6,165,199 A | 12/2000 | Barbut | |
| 6,277,139 B1 | 8/2001 | Levinson et al. | |
| 6,336,934 B1 | 1/2002 | Gilson et al. | |
| 6,383,205 B1 | 5/2002 | Samson et al. | |
| 6,443,926 B1 | 9/2002 | Kletschka | |
| 6,485,456 B1 | 11/2002 | Kletschka | |
| 6,485,500 B1 | 11/2002 | Kokish et al. | |
| 6,491,712 B1 | 12/2002 | O'Connor | |
| 6,511,503 B1 | 1/2003 | Burkett et al. | |

(Continued)

FOREIGN PATENT DOCUMENTS

| | | |
|---|---|---|
| EP | 0 200 668 A2 | 12/1986 |
| GB | 1 588 072 A1 | 1/1978 |

*Primary Examiner* — Melanie Tyson
(74) *Attorney, Agent, or Firm* — Vista IP Law Group LLP

(57) ABSTRACT

Devices, systems and methods for removing foreign bodies within a body lumen are disclosed. An unfolding balloon catheter may include an elongated shaft having an intussuscepting balloon that can be actuated within a body lumen to capture and retrieve an intravascular device. The balloon may be configured to radially and/or axially expand when inflated, enveloping the intravascular device. In certain embodiments, the balloon may be formed by folding the ends of a distensible member inwardly, and then bonding the ends of the distensible member to the elongated shaft to form an expandable sleeve. An adhesive layer located along a portion of the elongated shaft may be used to temporarily secure the balloon to the elongated shaft.

32 Claims, 13 Drawing Sheets

U.S. PATENT DOCUMENTS

| | | |
|---|---|---|
| 6,527,790 B2 | 3/2003 | Chien et al. |
| 6,544,279 B1 | 4/2003 | Hopkins et al. |
| 6,569,182 B1 | 5/2003 | Balceta et al. |
| 6,569,184 B2 | 5/2003 | Huter |
| 6,589,263 B1 | 7/2003 | Hopkins et al. |
| 6,592,616 B1 | 7/2003 | Stack et al. |
| 6,596,011 B2 | 7/2003 | Johnson et al. |
| 6,607,506 B2 | 8/2003 | Kletschka |
| 6,616,676 B2 * | 9/2003 | Bashiri et al. .............. 606/159 |
| 6,616,679 B1 | 9/2003 | Khosravi et al. |
| 6,635,070 B2 | 10/2003 | Leeflang et al. |
| 2003/0176910 A1 * | 9/2003 | Vrba et al. ................ 623/1.11 |

* cited by examiner

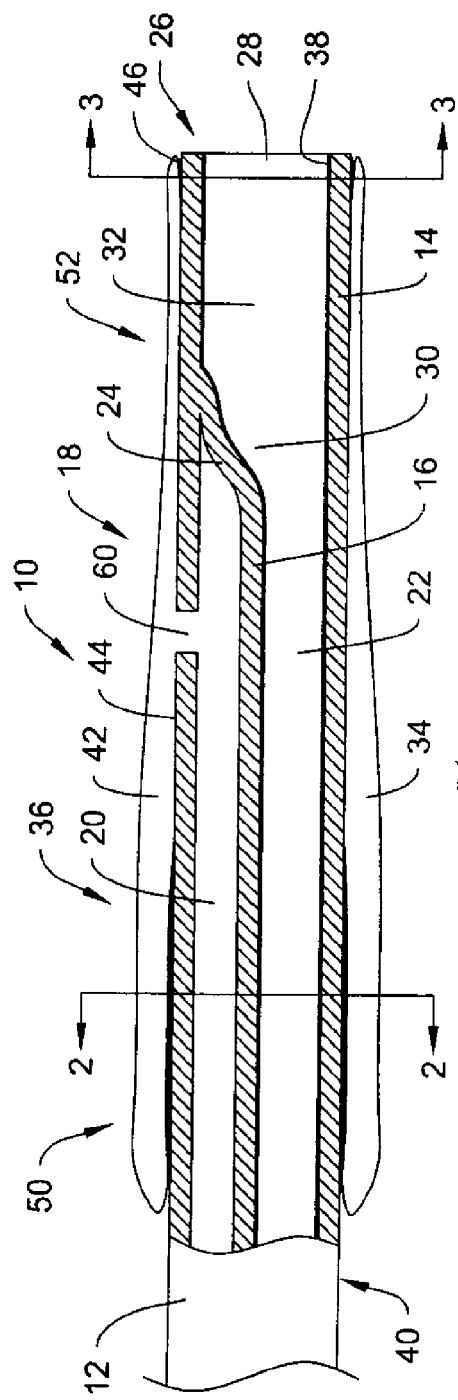
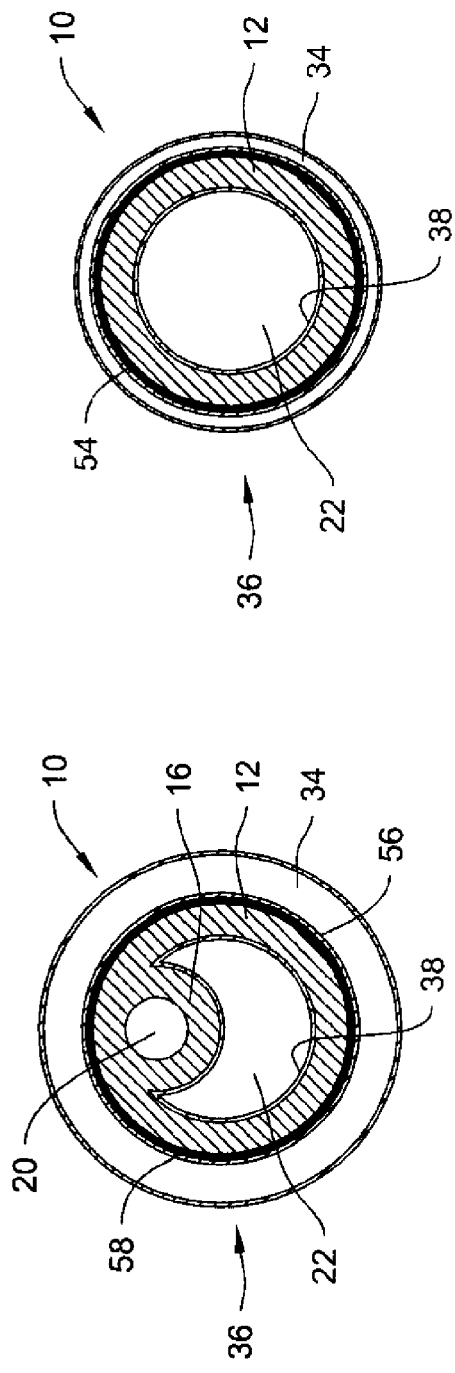

US 8,444,661 B2

UNFOLDING BALLOON CATHETER FOR PROXIMAL EMBOLUS PROTECTION

This application is a continuation application of U.S. application Ser. No. 10/690,004, filed Oct. 21, 2003.

FIELD OF THE INVENTION

The present invention relates generally to the field of intravascular devices. More specifically, the present invention pertains to catheter devices for proximal embolus protection within a body lumen.

BACKGROUND OF THE INVENTION

Embolectomy devices such as inflatable catheters and clot pullers are used in a variety of applications to remove blood clots or other foreign bodies from a blood vessel such as an artery or vein. The formation of thrombus within the vessel may partially block or totally occlude the flow of blood through the vessel, preventing the flow of blood downstream to vital locations within the body. Such thrombolytic events may also be exacerbated by atherosclerosis, a vascular disease that causes the vessels to become tortuous and narrowed. The tortuousness or narrowness of the vessel may, in certain circumstances, lead to the formation of atherosclerotic plaque, which can cause further complications in the body.

In embolectomy procedures for removing such blood clots from the body, a delivery catheter or sheath is typically inserted percutaneously into the body (e.g. via the femoral, jugular or antecubital veins) and advanced to a target site within the body containing the clot. To ascertain the precise location of the blood clot within the body, radiopaque die may be injected into the body permitting the occluded blood vessel to be radiographically visualized with the aid of a fluoroscope. A Fogarty catheter or other suitable delivery device may be used to transport the embolectomy device in a collapsed position distal the site of the clot. The embolectomy device is then withdrawn from within the delivery device, causing the device to expand within the vessel. The embolectomy device may then be urged in the proximal direction to remove the clot from the vessel wall. A wire basket, coil, membrane or other collector element can be used to capture the clot as it is dislodged from the vessel wall. Once entrained within the collector element, the embolectomy device and captured blood clot are then loaded into a retrieval device and withdrawn from the patient's body.

In certain applications, the removal of the foreign object within the vessel may cause emboli to migrate upstream and enter other branching passageways within the body. To prevent migration of emboli upstream, it may be necessary to temporarily impede or obstruct the flow of blood proximal the therapeutic site while retrieving the embolectomy device.

SUMMARY OF THE INVENTION

The present invention pertains to catheter devices for proximal embolus protection within a body lumen. An unfolding balloon catheter in accordance with an exemplary embodiment of the present invention includes an intussuscepting balloon disposed about the distal section of an elongated shaft. An inflation lumen extending through a portion of the elongated shaft may be configured to deliver pressurized fluid through an orifice in the external wall of the elongated shaft to the interior of the intussuscepting balloon.

The intussuscepting balloon may be configured to radially expand to partially or fully occlude the body lumen proximal the intravascular device. The intussuscepting balloon may be formed by folding the ends of a distensible member inwardly, and then securing the ends of the distensible member to the elongated shaft to form an expandable sleeve. An adhesive layer located about a portion of the elongated shaft may be used to temporarily secure a portion of the intussuscepting balloon to the outer periphery of the elongated shaft. In use, pressurized fluid can be delivered through the inflation lumen to inflate the balloon within the vessel. Once the pressure within the expandable sleeve reaches a pre-defined level, the balloon may be configured to unfold along the adhesive layer and envelope the intravascular device. In certain embodiments, a retrieval lumen operatively coupled to a vacuum source may be employed to aspirate the intravascular device and/or foreign object at least in part into the catheter.

BRIEF DESCRIPTION OF THE DRAWINGS

FIG. 1 is a partial cross-sectional view of an unfolding balloon catheter in accordance with an exemplary embodiment of the present invention;

FIG. 2 is a cross-sectional view of the elongated shaft along line 2-2 illustrated in FIG. 1;

FIG. 3 is a cross-sectional view of the elongated shaft along line 3-3 illustrated in FIG. 1;

DETAILED DESCRIPTION OF THE DRAWINGS

Figure 4:
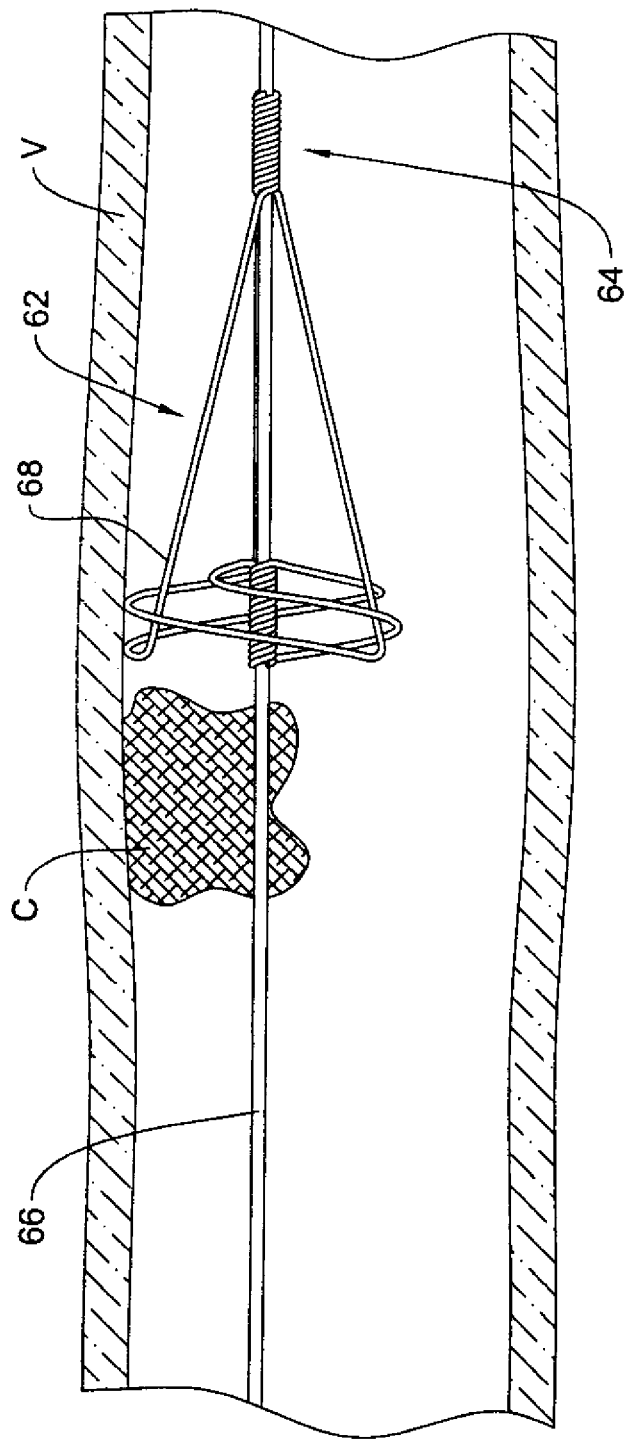
FIG. 4 is a partial cross-sectional view of an intravascular device advanced to a target site within a blood vessel.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

FIG. 1 is a perspective view of an unfolding balloon catheter 10 in accordance with an exemplary embodiment of the present invention. Unfolding balloon catheter 10 includes an elongated shaft 12 having an exterior wall 14, an interior wall 16, a distal section 18, and a proximal section (not shown) extending to a location outside of the body. As shown in FIG. 1, the interior wall 16 of the elongated shaft 12 divides the interior of the catheter 10, forming an inflation lumen 20 and a retrieval lumen 22. The inflation lumen 20 extends from the proximal section of the elongated shaft 12 to a closure 24 at or near the distal end 26 of the catheter 10. The retrieval lumen 22 extends from the proximal section of the elongated shaft 12 to an opening 28 formed through the distal end 26 of the catheter 10. At location 30, the retrieval lumen 22 transforms from a crescent shape to a substantially circular shape, forming a flared region 32 wherein the internal dimension of the retrieval lumen 22 increases slightly. As will be described in greater detail below, a source of pressurized fluid may be delivered through the inflation lumen 20 to the interior 34 of an intussuscepting balloon 36 to capture and retrieve an intravascular device.

The dimensions and general configuration of the balloon catheter 10 may vary depending on such factors as the location of the body to be traversed, the size of the target vessel, and the type of intravascular device to be retrieved. In applications involving the removal of blood clots using clot pullers or embolic protection filters, for example, the retrieval lumen 22 may include an inside diameter in the range of about 0.016 to 0.022 inches, although other sizes may be employed, as desired. In certain embodiments, the balloon catheter 10 may be configured similar to a microcatheter or guide catheter, allowing the catheter 10 to be used to both deliver and retrieve the intravascular device within the body. Although the illustrative elongated shaft 12 depicted in FIGS. 1-3 has a substantially circular profile, it should be understood that other shapes may be employed, if desired.

The elongated shaft 12 may be fabricated from polymeric and/or metallic materials using known PVS catheter techniques in the art. Examples of suitable materials may include, for example, stainless steel, nickel-titanium alloy, polyethylene terapthalate (PET), polytetraflouroethylene (PTFE), polyurethane, fluorinated ethylene propylene (FEP), polypropylene (PP), polyvinylchloride (PVC), polyetherether ketone (PEEK), polyimide, polyester, polyamide, elastomeric polyamides, block polyamide/ethers, polyether block amide (PEBAX), and polyetherimide (PEI).

In certain embodiments, all or portions of balloon catheter 10 may include a lubricious coating. For example, as shown in FIG. 1, a thin layer 38 of lubricious material may be placed on all or a portion of the interior of the retrieval lumen 22 to facilitate retrieval of an intravascular device. Other coatings such as hydrophilic or protective coatings may also be applied to the retrieval lumen 22 as well as other locations along the catheter 10, as desired. Examples of such coatings and materials, including methods used to create such coatings, can be found in U.S. Pat. Nos. 5,772,609 and 6,139,510, to Nguyen et al. and Palermo, respectively, which are incorporated herein by reference.

Balloon catheter 10, or portions thereof may also be coated, plated, wrapped or surrounded by, doped with, or otherwise include a radiopaque material. Radiopaque materials are understood to be materials capable of producing a relatively bright image on a fluoroscopic monitor or other imaging device, allowing the physician to determine the location of the balloon catheter 10 within the body. Some examples of radiopaque materials may include metals such as gold, platinum, palladium, tantalum, tungsten alloy, or materials loaded with a radiopaque filler such as barium sulfate, powdered tantalum, powdered tungsten, bismuth oxide, and the like.

In a deflated position depicted in FIG. 1, intussuscepting balloon 36 is configured to lie circumferentially adjacent the outer periphery 40 of the elongated shaft 12. The intussuscepting balloon 36 may be formed from a distensible member 42 configured to expand to a particular, pre-defined shape when inflated via inflation lumen 20. The distensible member 42 may be formed from a thin layer of polyethylene (PE), radiated polyethylene, polytetraflouroethylene (PTFE) or other suitable material having a proximal end 44 and a distal end 46 that are each bonded, fused, or otherwise secured to the elongated shaft 12, forming an expandable sleeve.

In certain embodiments, the intussuscepting balloon 36 may be formed by a folding process, wherein a proximal portion 50 of the distensible member 42 is folded inwardly such that the distensible member 42 is relatively slack at the proximal portion 50 when deflated. The distal portion 52 of the distensible member 42, in turn, may be relatively taut such that the distensible member 42 does not extend distally beyond the distal end 26 of the elongated shaft 12 in the deflated position. As shown in FIG. 3, a layer 54 of adhesive, cement or other suitable bonding agent may be placed about the elongated shaft 12 at or near the distal end 26 to relieve any slack along the distal portion 52 of the distensible member 42, thereby reducing the profile of the balloon 36.

As shown in FIG. 2, the folded portion 56 of the distensible member 42 may be removably secured to the outer periphery 40 of the elongated shaft 12 via an adhesive layer 58. The adhesive layer 58 may be configured to temporarily secure the proximal portion 50 of the distensible member 42 about the outer periphery 40 of the elongated shaft 12 to maintain a low profile when the balloon catheter 10 is transported through the body. During inflation of the intussuscepting balloon 36, the radial force inside the balloon causes the balloon 36 to expand, which counteracts the force maintained by the adhesive layer 58. At a sufficient pressure, the force resulting from the injection of inflation fluid into the intussuscepting balloon 36 overcomes the bonding force of the adhesive layer 58, causing the balloon 36 to unfold distally beyond the distal end 26 of the elongated shaft 12. In certain embodiments, the adhesive layer 58 can be configured to prevent the intussuscepting balloon 36 from unfolding until a sufficient pressure is reached, allowing the balloon 36 to first radially expand within the body before enveloping the intravascular device.

The amount and direction of expansion of the intussuscepting balloon 36 can also be controlled by the type of materials employed. In certain embodiments, for example, a non-compliant material may be used to limit the amount of expansion of the intussuscepting balloon 36 to a pre-defined size. In other embodiments, a compliant material may be employed, allowing further expansion of the intussuscepting balloon 36, if desired. In one exemplary embodiment, the intussuscepting balloon 36 may comprise a multiple-layered construction wherein the inner layer of the balloon 36 is generally thicker than the outer layer, biasing the balloon 36 to expand radially when inflated.

The inflation lumen 20 may be fluidly coupled to a source of pressurized fluid that can be used to selectively inflate or deflate the intussuscepting balloon 36. An orifice 60 formed through the external wall 14 of the elongated shaft 12 adjacent the inflation lumen 20 fluidly connects the interior 34 of the intussuscepting balloon 36 with the inflation lumen 20. The amount of inflation or deflation can be controlled using a pressure valve or other suitable mechanism connected to the proximal section of the elongated shaft 12. A radiopaque coating or material on the intussuscepting balloon 36 can be used to fluoroscopically monitor the amount of radial and/or axial expansion that has occurred within the body, if desired.

The retrieval lumen 22 may be operatively connected to a vacuum source to provide suction at the distal end 26 of the elongated shaft 12 to aspirate the intravascular device and any emboli into the balloon catheter 10. The flared region 32 of the retrieval lumen 22 may be configured to receive all or part of the intravascular device therein. In the illustrative embodiment depicted in FIG. 1, the location 30 where the retrieval lumen 22 transforms in size and shape may be used as a proximal stop, limiting proximal movement of the intravascular device into the crescent shaped portion of the retrieval lumen 22.

Figure 5:
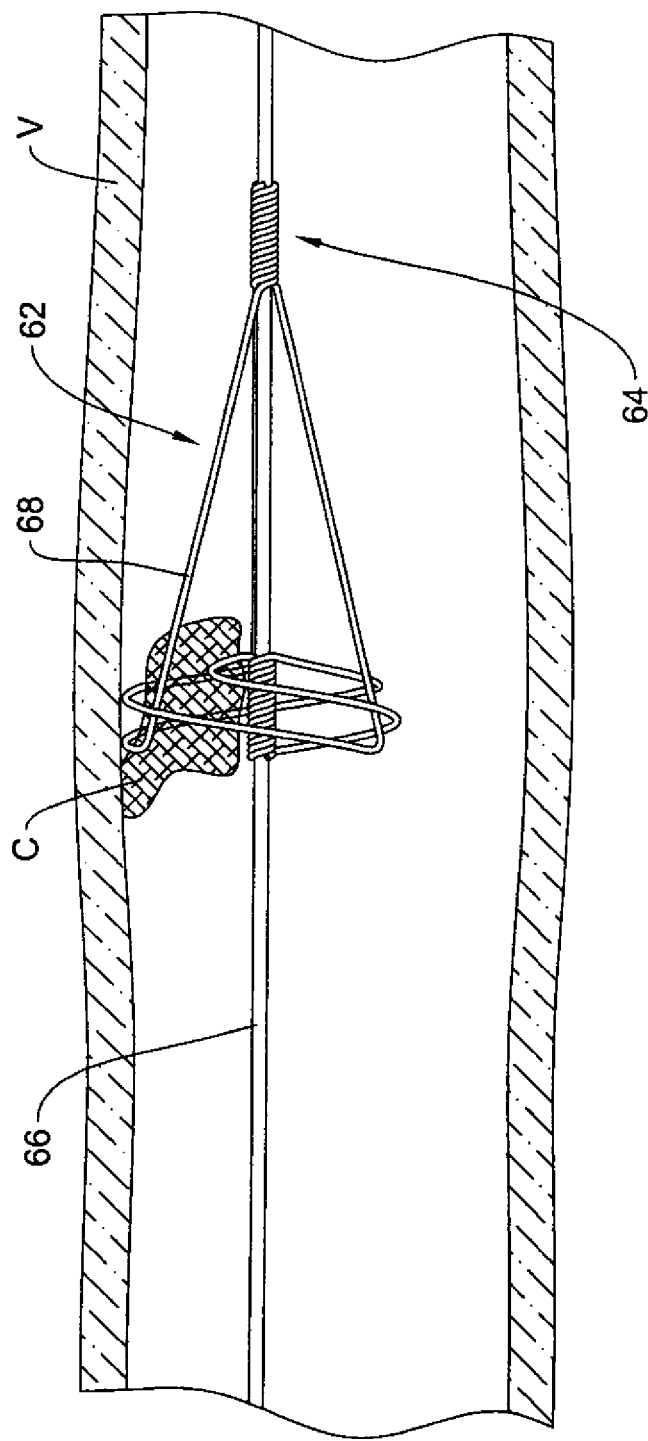
FIG. 5 is a partial cross-sectional view of the intravascular device of FIG. 4, wherein the intravascular device is shown engaged along the wall of the blood vessel.

Referring now to FIGS. 4-9, an exemplary method of retrieving a foreign object within a blood vessel will now be described with respect to the unfolding balloon catheter 10 illustrated in FIGS. 1-3 and described herein. As shown in FIG. 4, an illustrative clot puller 62 coupled to the distal portion 64 of a guidewire 66 may be advanced to a location with a blood vessel V distal a blood clot C or other foreign object. Clot puller 62 may include a wire basket 68 or other suitable collection mechanism configured to capture and retrieve the blood clot C. To dislodge the blood clot C from the wall of the blood vessel V, the operator can retract the guidewire 66 proximally a distance, engaging the clot puller 62 along the wall of the blood vessel V. Continued retraction of the clot puller 62 in the proximal direction causes the blood clot C to become severed from the vessel wall and enter the wire basket 68, as shown in FIG. 5.

Figure 6:
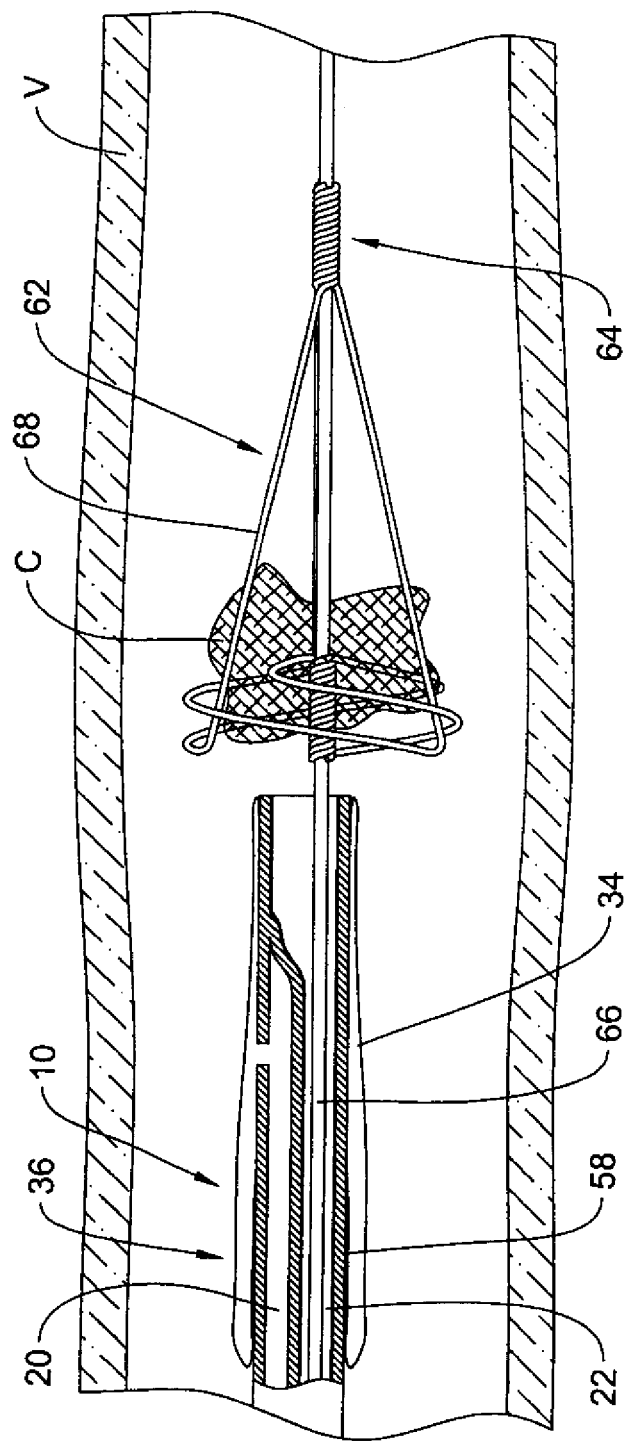
FIG. 6 is a partial cross-sectional view showing an exemplary unfolding balloon catheter advanced to the target site of the blood vessel, wherein the balloon catheter is shown in a deflated state.
Figure 7:
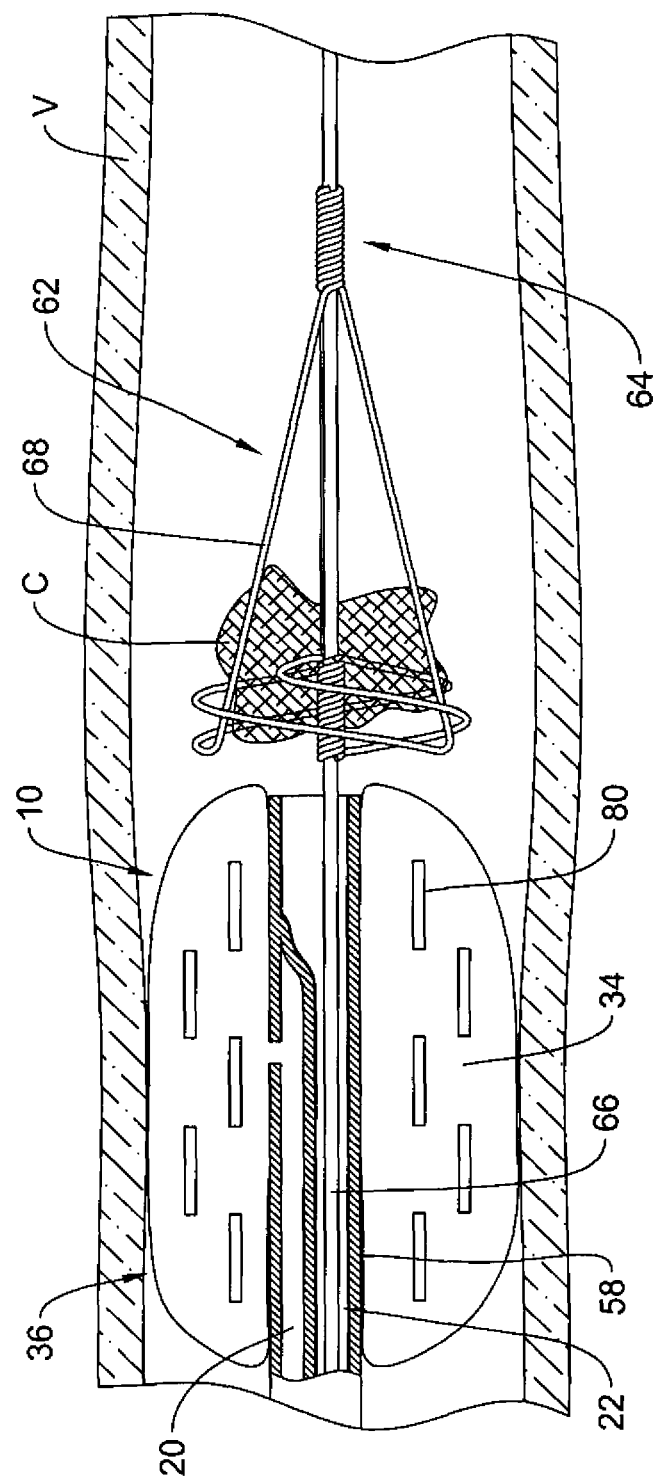
FIG. 7 is a partial cross-sectional view of the unfolding balloon catheter of FIG. 6, wherein the balloon catheter is shown in a partially inflated state.

As shown in FIG. 6, unfolding balloon catheter 10 may be advanced along the guidewire 66 and positioned adjacent to the clot puller 62 with the aid of a fluoroscope or other suitable visualization means. Once positioned, fluid may be delivered through inflation lumen 20 and into the intussuscepting balloon 36, causing the balloon 36 to initially expand in a radial direction and dilate the vessel wall, as shown in FIG. 7. In this stage, the proximal flow of blood may be partially or totally occluded to prevent emboli dislodged during the embolectomy procedure from migrating proximally into a branching vessel or other location within the body.

Figure 8:
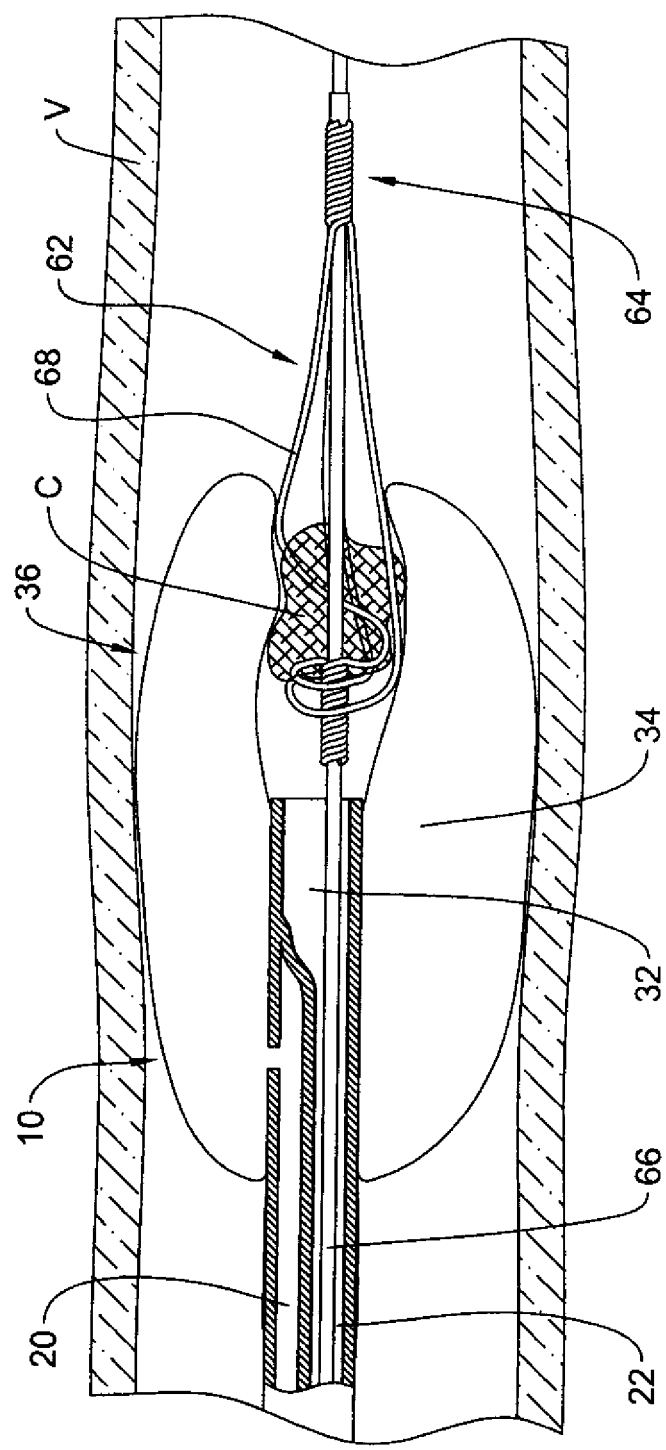
FIG. 8 is a partial cross-sectional view of the unfolding balloon catheter of FIG. 6, wherein the balloon catheter is shown in a fully inflated position intussuscepted about the intravascular device.

As the pressure within the interior 34 of the intussuscepting balloon 36 increases, the radial force will eventually exceed the bonding force of the adhesive layer 58. When this occurs, the intussuscepting balloon 36 unfolds and begins to envelope the proximal portion of the clot puller 62, as shown in FIG. 8. The axial force of the intussuscepting balloon 36 exerted along the wall of the blood vessel V as it unfolds tends to shear any remaining portion of the blood clot C along the vessel wall. The intussuscepting balloon 36 may be inflated sufficiently to envelope the clot puller 62 without imparting pressure on the incoming blood clot C, thus preventing fragmentation of the blood clot C. The particular shape of the intussuscepting balloon 36 can, of course, be configured to assume a certain shape depending on the particular application.

Inflation of the balloon catheter 10 may be accomplished at any time during the embolectomy procedure. Thus, while the step of inflating the balloon catheter 10 in FIGS. 7-8 is illustratively performed subsequent to the step of engaging the clot puller 58 along the vessel wall, it should be understood that inflation may be timed to occur concurrently with, or prior to, engagement. In certain methods, for example, the intussuscepting balloon 36 may be inflated concurrently with the step of engaging the clot puller 62 proximally along the vessel wall.

The intussuscepting balloon 36 can be configured to fully appose the vessel wall, temporarily restricting the flow of blood within the vessel, or can be configured to occlude only a portion of the vessel, as desired. In certain embodiments, the portion of the intussuscepting balloon 36 that contacts and engages the walls of the vessel may include one or more cutting edges or blades 80 configured to remove the blood clot C from the vessel wall. The cutting edges or blades 80 may be placed circumferentially about the outer periphery of the intussuscepting balloon 36, and can be configured to engage the vessel wall when the balloon 36 is axially expanded within the blood vessel V. Alternatively, or in addition, the cutting edges or blades 80 may be placed longitudinally along the length of the intussuscepting balloon 36, and can be configured to engage the vessel wall by rotation of the elongated shaft 12 within the blood vessel V.

Figure 9:
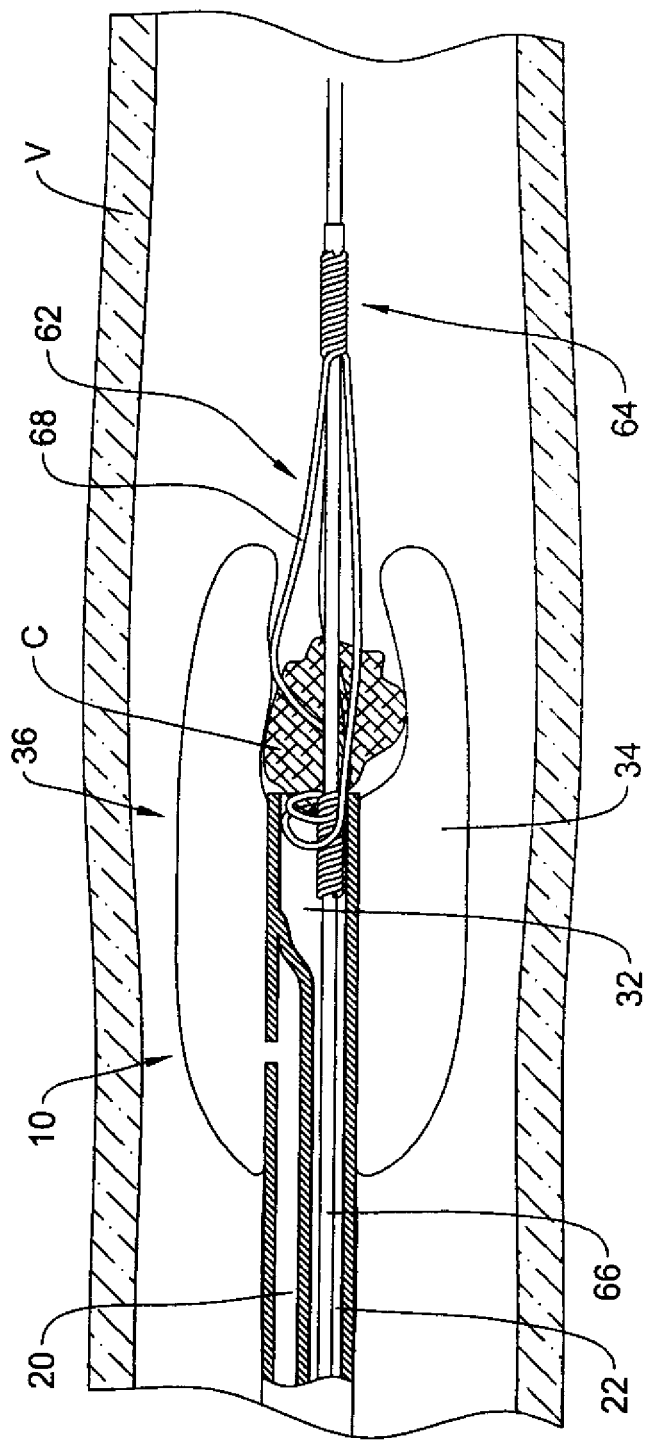
FIG. 9 is a partial cross-sectional view of the unfolding balloon catheter of FIG. 6, wherein the intravascular device is disposed at least in part within the retrieval lumen of the balloon catheter.

Once enveloped at least in part within the intussuscepting balloon 36, the clot puller 62 and accompanying blood clot C can then be loaded at least in part into the retrieval lumen 22 for removal from the body. In certain embodiments, a vacuum source coupled to the retrieval lumen 22 may be used to provide suction at the distal end 26 of the catheter 10, aspirating the clot puller 62 at least in part into the flared region 32 of retrieval lumen 22, as shown in FIG. 9. Alternatively, or in addition, the physician may retract the guidewire 66 in the proximal direction, causing the clot puller 62 and captured blood clot C to be drawn into the flared region 32 of the retrieval lumen 22. During aspiration and/or retraction, the intussuscepting balloon 36 may be deflated slightly to permit the clot puller 62 to re-prolapse, if necessary.

Figure 10:
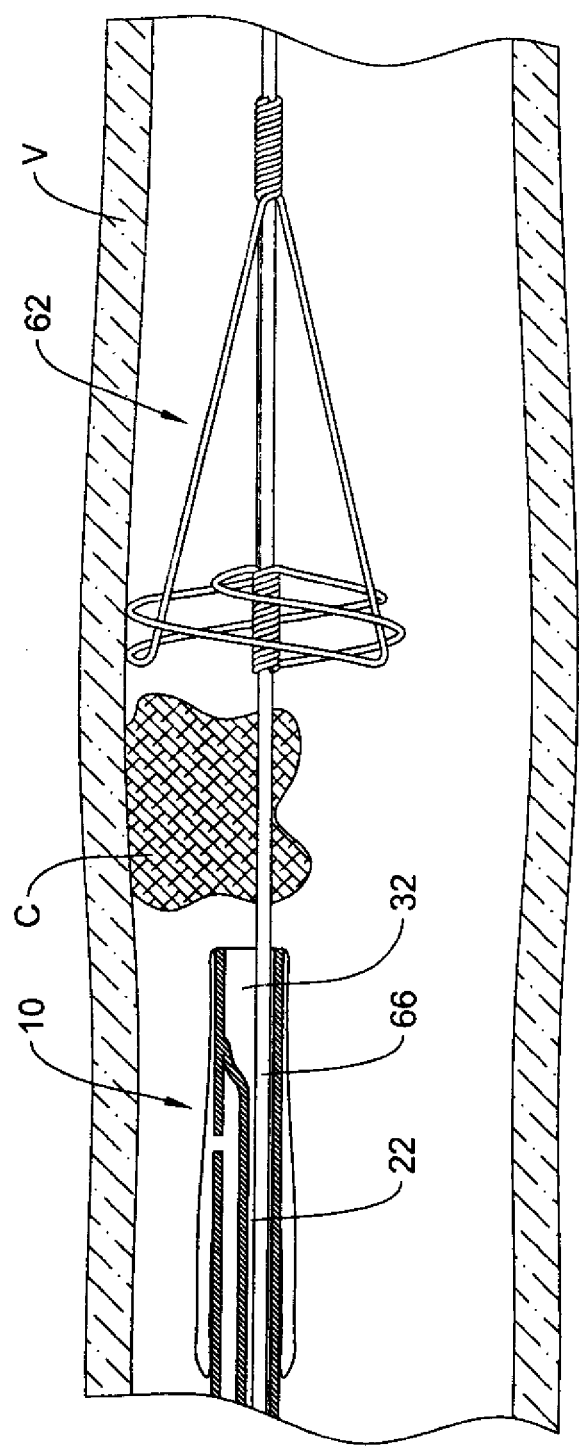
FIG. 10 is a partial cross-sectional view showing an exemplary unfolding balloon catheter and intravascular device advanced to a target site within a blood vessel.
Figure 11:
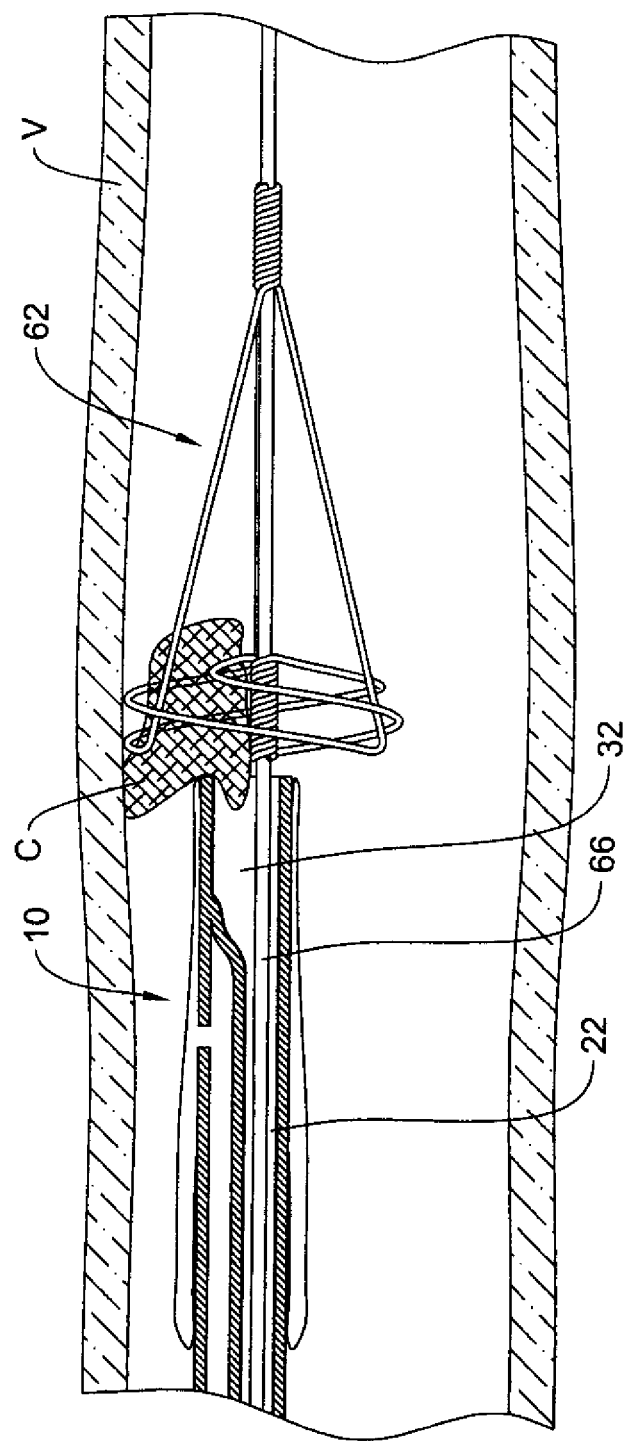
FIG. 11 is a partial cross-sectional view showing the unfolding balloon catheter and intravascular device of FIG. 10 engaged within the blood vessel.
Figure 12:
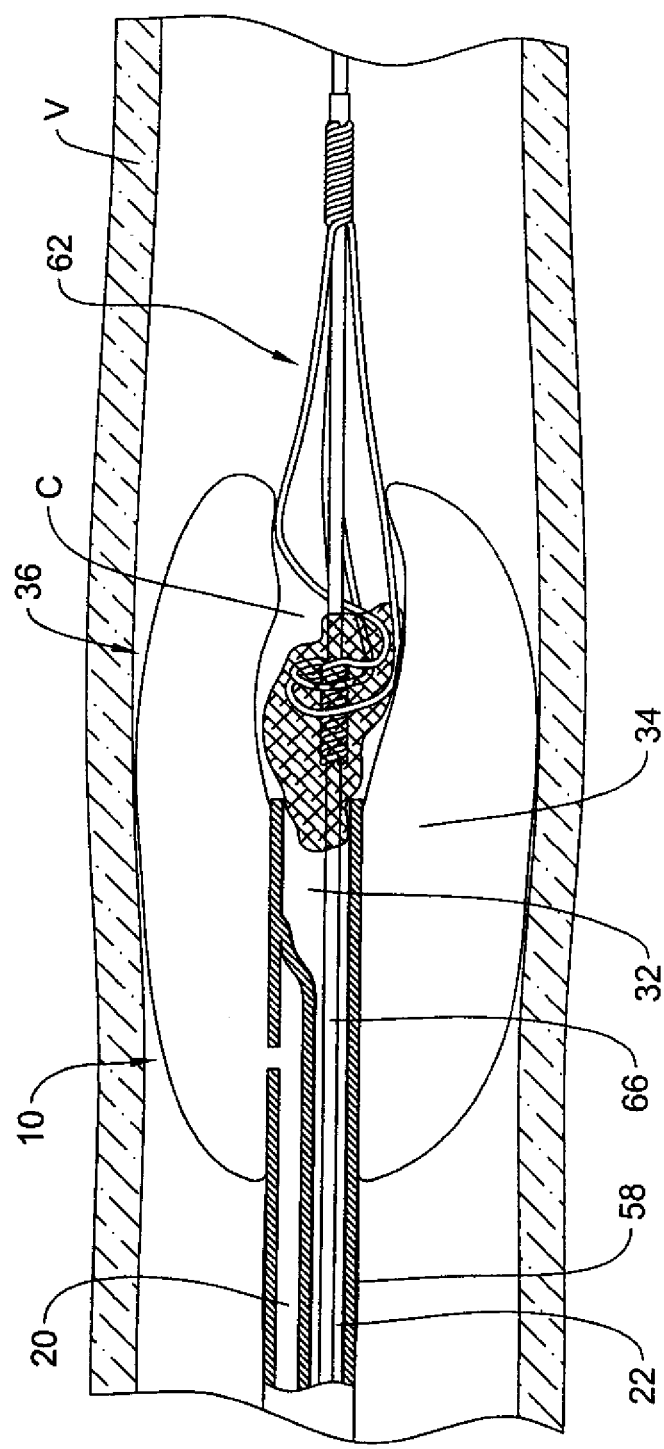
FIG. 12 is a partial cross-sectional view of the unfolding balloon catheter of FIG. 10, wherein the balloon catheter is shown in a fully inflated positioned intussuscepted about the intravascular device.

FIGS. 10-12 depict an alternative method of retrieving a foreign object within a blood vessel using the unfolding balloon catheter 10. As shown in FIG. 10, an intravascular device such as clot puller 62 described herein may be advanced via guidewire 66 to a location within a blood vessel V distal a blood clot C. The unfolding balloon catheter 10 can also be advanced along the guidewire 66 and positioned at a location within vessel V proximal the blood clot C. Advancement of the unfolding balloon catheter 10 may occur either subsequent to the placement of the clot puller 62 within vessel V, or concurrently with the placement of the clot puller 62.

Once the unfolding balloon catheter 10 and clot puller 62 have been advanced to the general location of the blood clot C, the physician next engages the unfolding balloon catheter 10 against the blood clot C by urging the catheter 10 forward slightly, or in the alternative retracting the guidewire proximally, causing the balloon catheter 10 to contact the blood clot C. A vacuum source coupled to the retrieval lumen 22 provides suction that can be used to aspirate the blood clot C at least in part into the flared region 32 of the retrieval lumen 22. With the blood clot C held tight against the catheter 10 vis-à-vis the vacuum source, the physician may urge the clot puller 62 in the proximal direction, causing the blood clot C to become severed from the wall of the vessel V and entrained within the clot puller 62, as shown in FIG. 11.

To intussuscept the clot puller 62 and blood clot C, fluid may be delivered through the inflation lumen 20 and into the intussuscepting balloon 36, causing the balloon 36 to initially expand in a radial direction within the vessel V. As the pressure within the interior 34 of the balloon 36 continues to increase, the radial force will eventually exceed the bonding force of the adhesive layer 58, causing the balloon 36 to unfold and envelope the proximal portion of the clot puller 62 and blood clot C, as shown in FIG. 12. The axial force of the intussuscepting balloon 36 exerted on the wall of the blood vessel V as it unfolds tends to shear any remaining portion of the blood clot C along the vessel wall.

Figure 13:
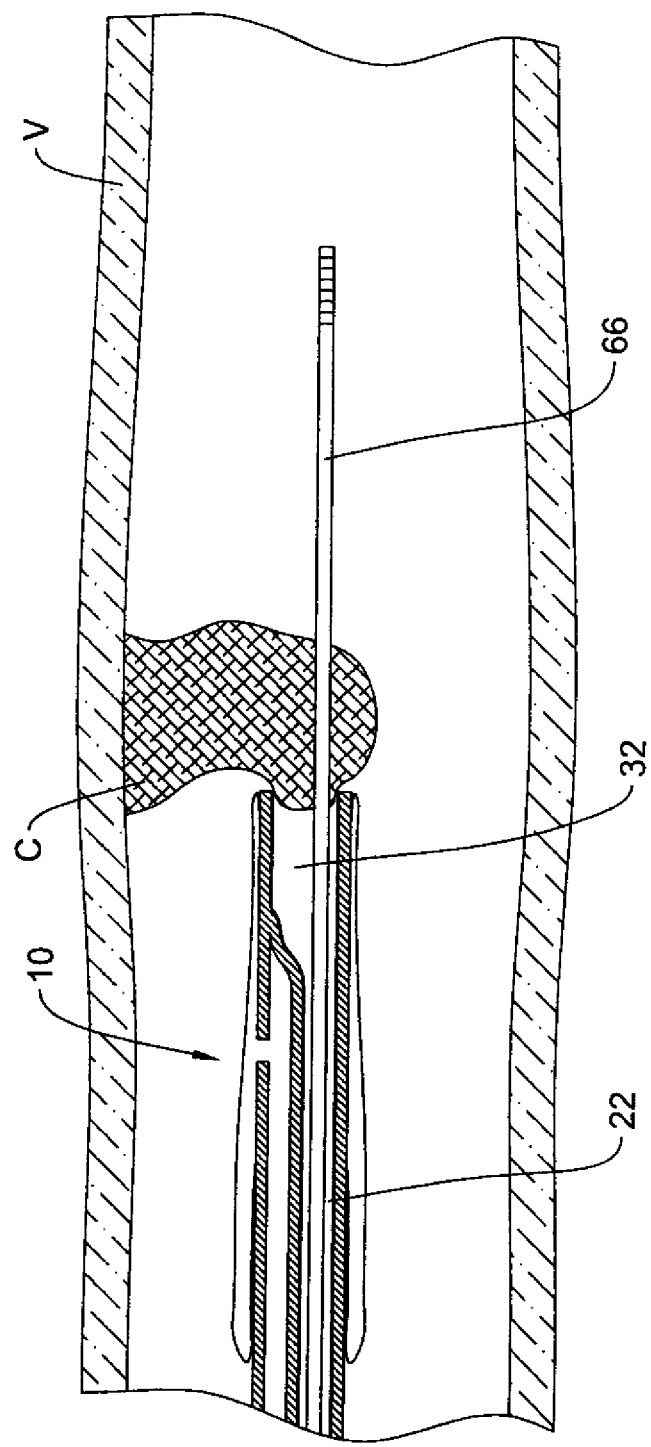
FIG. 13 is a partial cross-sectional view showing an exemplary unfolding balloon catheter advanced to a target site within a vessel and engaged at a blood clot, wherein the balloon catheter is shown in a deflated state.
Figure 14:
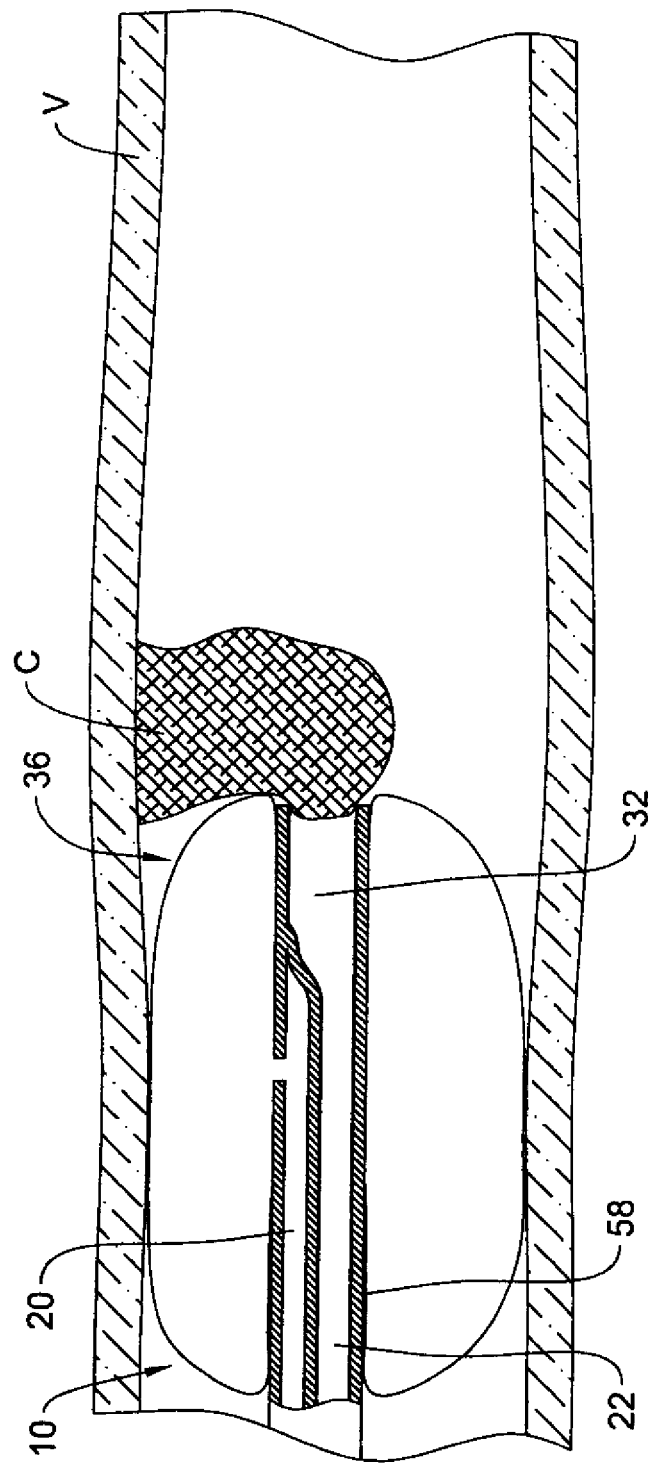
FIG. 14 is a partial cross-sectional view of the unfolding balloon catheter of FIG. 13, wherein the balloon catheter is shown in a partially inflated state.
Figure 15:
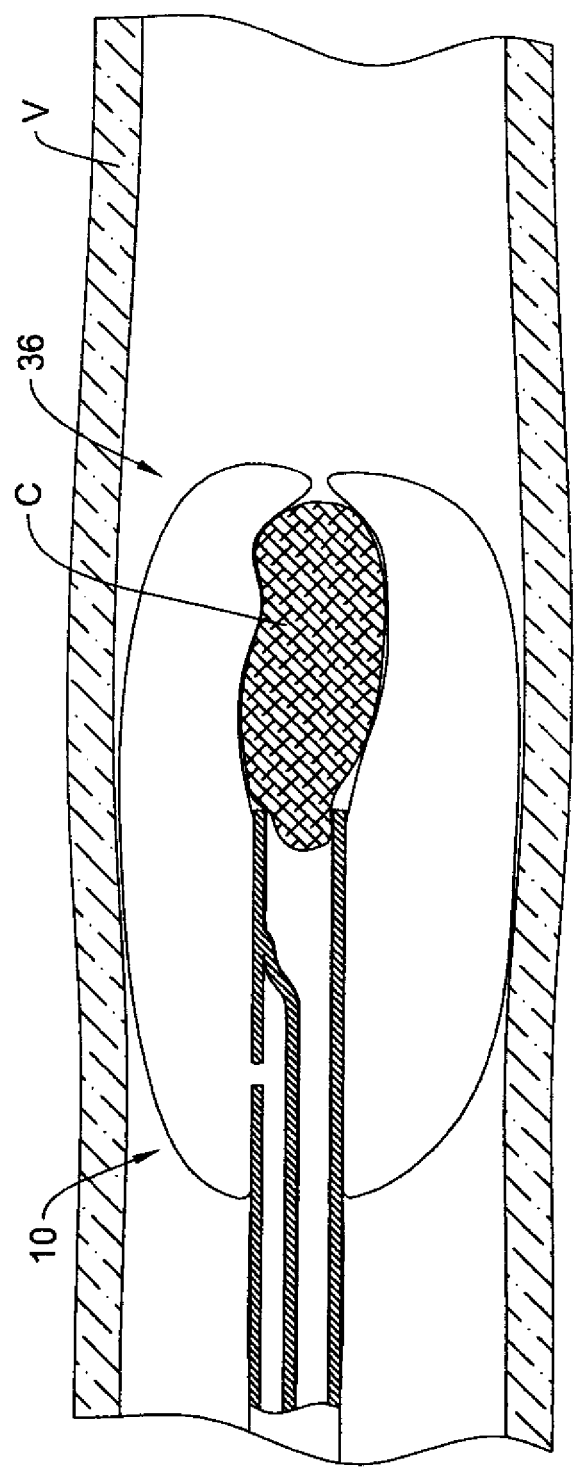
FIG. 15 is a partial cross-section view of the unfolding balloon catheter of FIG. 13, wherein the balloon catheter is shown in a fully inflated state intussuscepted about the blood clot.

FIGS. 13-15 depict another alternative method of retrieving a foreign object within a blood vessel using only the unfolding balloon catheter 10. As shown in FIG. 13, the unfolding balloon catheter 10 may be advanced along guidewire 66 and engaged at a location within a blood vessel V proximal a blood clot C. With the unfolding balloon catheter 10 engaged against the blood clot C, the physician can then remove the guidewire 66 and activate a vacuum source coupled to the retrieval lumen 22 to aspirate the blood clot C at least in part within the flared region 32 of retrieval lumen 22.

To intussuscept the blood clot C, fluid may be delivered through the inflation lumen 20 and into the intussuscepting balloon 36, causing the balloon 36 to initially expand in a radial direction within the vessel V, as shown in FIG. 14. As the pressure within the balloon 36 continues to increase, the radial force will eventually exceed the bonding force of the adhesive layer 58, causing the balloon 36 to unfold and shear the blood clot C from the vessel wall. Once removed from the vessel wall, the intussuscepting balloon 36 can be configured to envelope the blood clot C, as shown in FIG. 15.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention. While the present invention has been described with respect to the extraction of blood clots during an embolectomy procedure, it should be understood that the present invention may be used in other applications, if desired.

What is claimed is:

1. A medical device for retrieving a foreign object within a body lumen, comprising:
   an intravascular device configured to capture a foreign object within a body lumen;
   an elongated shaft having a proximal section and a distal section;
   an inflation lumen extending from the proximal section of the elongated shaft to the distal section of the elongated shaft; and
   an expandable sleeve having a proximal end and a distal end bonded to the distal section of the elongated shaft and in fluid communication with the inflation lumen, wherein a portion of the expandable sleeve is removably secured to the elongated shaft by an adhesive layer disposed about a portion of the elongated shaft and is configured to release from and unfold along the adhesive layer as the balloon unfolds distally beyond the distal section of the elongated shaft as it begins to envelop a proximal portion of the intravascular device, thereby retrieving the intravascular device.

2. The medical device of claim 1, further comprising a retrieval lumen extending from the proximal section of the elongated shaft to an opening at the distal section of the elongated shaft.

3. The medical device of claim 2, wherein the retrieval lumen includes a distal flared region.

4. The medical device of claim 2, wherein the retrieval lumen is operatively coupled to a vacuum source.

5. The medical device of claim 2, wherein the retrieval lumen includes a lubricious coating.

6. The medical device of claim 1, wherein the inflation lumen includes an inflation port disposed through an external wall of the elongated shaft.

7. The medical device of claim 1, wherein the inflation lumen is operatively coupled to a pressure source.

8. The medical device of claim 1, wherein the expandable sleeve is configured to unfold along the adhesive layer when inflated to a sufficient pressure.

9. The medical device of claim 1, wherein the expandable sleeve is configured to radially and axially expand to a predefined shape when inflated to a sufficient pressure.

10. The medical device of claim 1, wherein the expandable sleeve is formed of a non-compliant material.

11. The medical device of claim 1, wherein the expandable sleeve is formed of a compliant material.

12. The medical device of claim 1, wherein the expandable sleeve is formed at least in part of polyethylene.

13. The medical device of claim 1, wherein the expandable sleeve includes an inner layer and an outer layer.

14. The medical device of claim 13, wherein the inner layer of the expandable sleeve is thicker than the outer layer of the expandable sleeve.

15. The medical device of claim 13, wherein the expandable sleeve includes cutting means.

16. The medical device of claim 15, wherein said cutting means comprises at least one cutting blade or edge.

17. The medical device of claim 1, wherein said intravascular device is a clot puller.

18. A medical device for retrieving a foreign object within a body lumen while preventing proximal embolus flow, comprising:
   an intravascular device configured to capture a foreign object in a body lumen;
   an elongated shaft having a proximal section, a distal section, and an external wall;
   an inflation lumen extending from the proximal section of the elongated shaft to the distal section of the elongated shaft, the inflation lumen including an inflation port disposed through the external wall of the elongated shaft;
   an expandable sleeve having a proximal end and a distal end bonded to the distal section of the elongated shaft and in fluid communication with the inflation lumen; wherein a portion of the expandable sleeve is removably secured to the elongated shaft by an adhesive layer disposed about a portion of the elongated shaft and is configured to release from and unfold along the adhesive layer as the balloon unfolds distally beyond the distal section of the elongated shaft as it begins to envelop the proximal portion of the intravascular device thereby retrieving the intravascular device; and
   a retrieval lumen extending from the proximal section of the elongated shaft to an opening at the distal section of the elongated shaft.

19. The medical device of claim 18, wherein the retrieval lumen includes a distal flared region.

20. The medical device of claim 18, wherein the retrieval lumen is operatively coupled to a vacuum source.

21. The medical device of claim 18, wherein the retrieval lumen includes a lubricious coating.

22. The medical device of claim 18, wherein the inflation lumen is operatively coupled to a pressure source.

23. The medical device of claim 18, wherein the expandable sleeve is configured to unfold along the adhesive layer when inflated to a sufficient pressure.

24. The medical device of claim 18, wherein the expandable sleeve is configured to radially and axially expand to a pre-defined shape when inflated to a sufficient pressure.

25. The medical device of claim 18, wherein the expandable sleeve is formed of a non-compliant material.

26. The medical device of claim 18, wherein the expandable sleeve is formed of a compliant material.

27. The medical device of claim 18, wherein the expandable sleeve is formed at least in part of polyethylene.

28. The medical device of claim 18, wherein the expandable sleeve includes an inner layer and an outer layer.

29. The medical device of claim 28, wherein the inner layer of the expandable sleeve is thicker than the outer layer of the expandable sleeve.

30. The medical device of claim 28, wherein the expandable sleeve includes cutting means.

31. The medical device of claim 30, wherein said cutting means comprises at least one cutting blade or edge.

32. The medical device of claim 18, wherein said intravascular device is a clot puller.

\* \* \* \* \*

UNITED STATES PATENT AND TRADEMARK OFFICE
CERTIFICATE OF CORRECTION

PATENT NO. : 8,444,661 B2
APPLICATION NO. : 11/770023
DATED : May 21, 2013
INVENTOR(S) : Nair et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1328 days.

Signed and Sealed this
Eleventh Day of November, 2014

Michelle K. Lee
*Deputy Director of the United States Patent and Trademark Office*